US005858348A

United States Patent [19]

Matsuda et al.

[11] Patent Number: 5,858,348

[45] Date of Patent: Jan. 12, 1999

[54] PERFUME COMPOSITION CONTAINING (4R)-CIS-4-METHYL-2-SUBSTITUTED-TETRAHYDRO-2H-PYRAN DERIVATIVE AND METHOD FOR IMPROVING FRAGRANCE BY USING (4R)-CIS-4-METHYL-2-SUBSTITUTED-TETRAHYDRO-2H-PYRAN DERIVATIVE

[75] Inventors: Hiroyuki Matsuda; Takeshi Yamamoto, both of Kanagawa, Japan

[73] Assignee: Takasago International Corporation, Tokyo, Japan

[21] Appl. No.: 731,278

[22] Filed: Oct. 11, 1996

[30] Foreign Application Priority Data

Oct. 13, 1995 [JP] Japan .................................... 7-291932

[51] Int. Cl.$^{6}$ .................................................. A61K 31/765

[52] U.S. Cl. .......................... 424/78.38; 512/11; 549/356

[58] Field of Search .............................. 549/356; 512/11; 424/78.38

[56] References Cited

U.S. PATENT DOCUMENTS 3,161,657 12/1964 Eschenmoser et al. ................ 549/356

OTHER PUBLICATIONS

Perfume and Flavor Chemicals II, 2809 (1969).

G. Ohloff, *Olfaction and Taste*, vol. 4, 156 (1972), "Odorous Properties of Enantiomeric Compounds".

G. Schindler and F. Vogel, *Perfumer & Flavorist*, vol. 11, Jun./Jul. 29 (1986), "Dihydroroseoxide—A Unique New Aroma Chemical".

*Primary Examiner*—Terressa Mosley

*Attorney, Agent, or Firm*—Sughrue, Mion, Zinn, Macpeak & Seas, PLLC

[57] ABSTRACT

A perfume composition which contains a (4R)-cis-4-methyl-2-substituted-tetrahydro-2H-pyran derivative represented by formula (I):

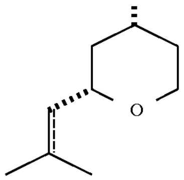

(I)

wherein ═══ represents a single or double bond, and a method for improving fragrance by using this perfume composition.

6 Claims, No Drawings

PERFUME COMPOSITION CONTAINING (4R)-CIS-4-METHYL-2-SUBSTITUTED-TETRAHYDRO-2H-PYRAN DERIVATIVE AND METHOD FOR IMPROVING FRAGRANCE BY USING (4R)-CIS-4-METHYL-2-SUBSTITUTED-TETRAHYDRO-2H-PYRAN DERIVATIVE

FIELD OF THE INVENTION

This invention relates to a perfume composition containing a (4R)-cis-4-methyl-2-substituted-tetrahydro-2H-pyran derivative, which has a high chemical purity and a high optical purity and can impart a refreshing, light and rose green feel to the fragrance of the perfume composition, and a method for improving a fragrance.

BACKGROUND OF THE INVENTION

4-Methyl-2-(2-methyl-1-propenyl)tetrahydro-2H-pyran (hereinafter sometimes referred to simply as rose oxide) is a compound which was found from Bulgarian rose oil in 1959 and occurs in essential oils of sweetbrier, geranium, lily, pelargonium, *Fatsia japonica,* gardenia, peppermint, etc., flavors of apricot, tomato, etc., and secretions of insects such as the musk long-horned beetle, etc.

Rose oxide has geometrical isomers and optical isomers and (4R)-cis- and trans-4-methyl-2-(2-methyl-1-propenyl) tetrahydro-2H-pyrans are found in natural plants such as roses and geraniums.

For the chemical synthesis of rose oxide, there have been known a method using β-citronellol as the starting material and another method using dihydropyrans as the starting materials.

In general, rose oxide has a refreshing, floral and green note. However, the fragrance delicately varies from isomer to isomer. That is to say, cis-rose oxide has a green note just like a geranium and peppermint, while trans-rose oxide has a somewhat intense fragrance compared with the cis-isomer [U.S. Pat. No. 3,161,657(1964)]. Further, it is described that (4R)-rose oxide has a sweet and floral fragrance with an intense green note while (4S)-rose oxide has a fragrance with a somewhat spicy note [*Perfume and Flavor Chemicals II,* 2809 (1969)]. It is also reported that rose oxide is usable in compounding various perfumes including rose and geranium based perfumes, since the addition of rose oxide in an amount of 0.05 to 0.5% imparts a light and floral top note to the perfumes [*Koryo* (*Perfume*), 178, 114 (June, 1993)]. However, the details are not stated relating to the all four individual optical isomers [*Olfaction and Taste,* 4, 156 (1972)].

It is reported that 4-methyl-2-(2-methylpropyl) tetrahydro-2H-pyran (hereinafter sometimes referred to as dihydrorose oxide) is synthesized from 3-methylbuten-3-ol-1 and 3-methylbutanal, and has a fragrance similar to that of rose oxide and is more stable to heat, acids and light than rose oxide, though nothing is stated relating to its optical isomers [*Perfumer & Flavarist,* 11, Jun./Jul. 29 (1986)].

With the recent diversification of perfumes and cosmetics, it has been required to develop a novel perfume material which is excellent in various characteristics (safety, stability, preference, freshness, natural feel, etc.) and has a good and intense fragrance. Accordingly, the present invention aims at providing a perfume composition containing a rose oxide which is capable of imparting a fresh, refreshing and rose green feel to a fragrance, and a method for improving a fragrance by which such a fragrance can be imparted.

SUMMARY OF THE INVENTION

The present inventors have conducted extensive studies in order to solve the above-mentioned problems. As a result, they have successfully found out that a (4R)-cis-4-methyl-2-substituted-tetrahydro-2H-pyran derivative having a chemical purity of at least 90% by weight and an optical purity of at least 95% ee sustains an intense fragrance, good fragrance qualities, a high biodegradability and a stimulative effect and that a perfume composition containing the same is useful as a perfume, thus completing the present invention.

DETAILED DESCRIPTION OF THE INVENTION

Now, the present invention will be described in greater detail.

Accordingly, the present invention is as follows.

1) A perfume composition which contains a (4R)-cis-4-methyl-2-substituted-tetrahydro-2H-pyran derivative represented by the following general formula (I):

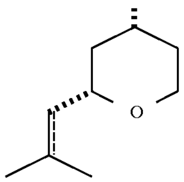

(I)

wherein ═══ represents a single or double bond.

2) A perfume composition as described in the above 1) wherein said (4R)-cis-4-methyl-2-substituted-tetrahydro-2H-pyran derivative has a chemical purity of at least 90% by weight and an optical purity of at least 95% ee.

3) A perfume composition as described in the above 1) or 2), wherein the content of said (4R)-cis-4-methyl-2-substituted-tetrahydro-2H-pyran derivative ranges from 0.01 to 30% by weight.

4) A method for improving a fragrance by using a (4R)-cis-4-methyl-2-substituted-tetrahydro-2H-pyran derivative represented by the general formula (I) given in the above 1).

The (4R)-cis-4-methyl-2-substituted-tetrahydro-2H-pyran derivative represented by the above general formula (I) to be used in the present invention includes the following 2 compounds:

(4R)-cis-4-methyl-2-(2-methyl-1-propenyl)tetrahydro-2H-pyran; and (4R)-cis-4-methyl-2-(2-methyl-propyl)tetrahydro-2H-pyran.

For example, these compounds can be synthesized from (S)-citronellol in accordance with the method described in JP-A-62-33134 (the term "JP-A" as used herein means an "unexamined published Japanese patent application").

Also, (S)-citronellol synthesized by the method described in *J.A.C.S.,* 109 1596 (1987) is brominated in the presence of sodium carbonate to thereby give a bromination product. Then it is debrominated with an acetonitrile solvent in the presence of Aliquat® (tricaprylylmethylammonium chloride) to give dehydrocitronellol which is subsequently cyclized with an acid catalyst. Thus, the target rose oxide is obtained.

Dihydrorose oxide can be obtained by hydrogenation of rose oxide with Raney nickel in a conventional manner. Then it may be further purified by distillation.

The fragrances of the above-mentioned compounds and isomers thereof, which will be described hereinafter, are checked by skilled panelists. The results are as follows.

Different from other isomers having herbal fragrances, cis-(2S,4R)-rose oxide has a floral green note as its basic fragrance with a clean, sharp, light and rose green note. Because of being highly diffusible and intense, the fragrance of this isomer is superior to those of others.

Different from other isomers having herbal fragrances, cis-(2R,4R)-dihydrorose oxide has a floral green note as its basic fragrance with a clean, light, ripe fruit, rose green and leafy note. Because of having the most intense fragrance, it is the best one among the isomers.

Among the isomers of rose oxide, a comparison on biodegradability indicates that the (4R)-isomers exclusively show biodegradability while the (4S)-isomers are hardly degradable. Between the (4R)-isomers, the cis-isomer degrades at a rate several times higher than that of the trans-isomer. These facts suggest that the (4R)-cis-isomer employed in the present invention is superior from the viewpoint of environment too. An examination on CNV indicates that the (4R)-isomers exclusively have stimulative effects.

In the perfume composition or the method for improving a fragrance according to the present invention, the content of the (4R)-cis-4-methyl-2-substituted-tetrahydro-2H-pyran derivative preferably ranges from 0.01 to 30% by weight. When its content is less than 0.01% by weight, only insufficient effect of imparting or improving a fragrance can be achieved. When its content exceeds 30% by weight, on the other hand, no further improvement in the effect can be obtained.

The perfume composition of the present invention is usable in order to impart or improve the fragrance of various products including hair care products (shampoo, rinse, perfume, hair cologne, hair tonic, hair cream, pomade, etc.), cosmetic bases and cosmetic cleansers (face powder, lipstick, etc.) and sanitary detergents (soap, kitchen detergent, laundry detergent, softener, disinfectant detergent, deodorizer, room aromatic, furniture care, disinfectant, bactericide, bleach, etc.).

The (4R)-cis isomers of rose oxide and dihydrorose oxide have each an intense fragrance and a preferable rose green note, compared with other isomers, and thus are highly preferable as a floral green perfume. By using these compounds, it is possible to prepare a fragrance composition having a highly preferable freshness, a refreshing feel and a rose green fragrance.

To further illustrate the present invention in greater detail, and not by way of limitation, the following Examples will be given.

The instruments employed in the following experiment are as follows.

[α]D: DIP-360 manufactured by JASCO Inc.
NMR: AMX-400 manufactured by Bruker, Inc.
MS: M-80B manufactured by Hitachi, Ltd.

[Method for determining chemical purity]

GC column: Neutrabond-1 (GL Science, 0.25 mm–30 m).
100° C. (0 min)–10° C./min–220° C. (0 min).

1) Rose oxide
cis: 4.72 min, trans: 4.93 min.

2) Dihydrorose oxide
cis: 4.04 min, trans: 4.35 min.

[Method for determining optical purity]

GC column: Chiraldex G-TA (manufactured by ASTEC) 0.25 mm–30 m.

1) Rose oxide
Conditions: 30° C. (20 min)–2° C./min –70° C. (40 min).

Retention time: cis-(2R,4S): 58.9 min.
cis-(2S,4R): 59.3 min.
trans-(2S,4S): 63.5 min.
trans-(2R,4R): 66.4 min.

2) Dihydrorose oxide
Conditions: 50° C. (constant temp.)
Retention time: cis-(2S,4S): 33.7 min.
cis-(2R,4R): 34.3 min.
trans-(2R,4S): 50.3 min.
trans-(2S,4R): 52.9 min.

SYNTHESIS EXAMPLE 1

Synthesis of cis-(2S,4R)-4-methyl-2-(2-methyl-1-propenyl)tetrahydro-2H-pyran (rose oxide)

1) Synthesis of dehydrocitronellol

To 156.3 g (1 mol) of (S)-citronellol (manufactured by Takasago International Corporation, 98% ee) was added 1.56 g (1% by weight) of sodium carbonate. After purging with nitrogen, 156.8 g (0.98 mol) of bromine was slowly added thereto while maintaining the temperature at 10° to 15° C. After the completion of the reaction, 1.6 l of acetonitrile was added and 3.12 g of Aliquat® 336 (manufactured by Henkel) was added in a nitrogen gas stream. After adding 224 g (4 mol) of potassium hydroxide at room temperature, the reactions mixture was heated to 75° C. and stirred for 16 hours. Next, 56 g (1 mol) of potassium hydroxide was further added and the mixture was stirred for 8 hours. After the completion of the reaction, 500 ml of hexane was added and the mixture was neutralized with 500 ml of 5% hydrochloric acid. The hexane layer was separated out, washed with water, further washed successively with a saturated aqueous solution of sodium chloride thrice, a saturated aqueous solution of sodium hydrogencarbonate once and a saturated aqueous solution of sodium chloride once, and concentrated to thereby give 144 g of the product.

2) Synthesis of cis-(2S,4R)-rose oxide

To 144 g of the dehydrocitronellol obtained in the above 1) was added twice as much 30% diluted sulfuric acid at room temperature and the resulting mixture was stirred for 16 hours. After the completion of the reaction, the organic layer was neutralized with a saturated aqueous solution of sodium hydrogencarbonate and washed with a saturated aqueous solution of sodium chloride thrice. Then the organic layer was separated out, concentrated and distilled (75°–77° C./9 mmHg) to thereby give 73.1 g of the product.

Then this product was finely distilled at 73°–74° C./12 mmHg to thereby give 45.4 g of the purified product.

[α]D 24: −78.4° (c 1.2, $CHCl_3$).
$^1$H-NMR (400 MHz, $CDCl_3$, ppm):
0.93 (d, 3H), 1.02 (dt, 1H), 1.21 (ddd, 1H), 1.49–1.70 (m, 3H), 1.68 (d, 3H), 1.72 (d, 3H), 3.47 (ddd, 1H), 3.93–4.01 (m, 2H), 5.16 (m, 1H).
MS (m/e): 154 ($M^+$), 139, 83, 69, 55, 41, 39.
IR ($cm^{-1}$): 2925, 1680, 1375, 1090.

SYNTHESIS EXAMPLE 2

Synthesis of cis-(2R,4R)-dihydrorose oxide

To 100 g of the rose oxide produced in Synthesis Example 1 was added 200 ml of ethanol. After adding 0.5 g of Raney nickel, hydrogenation was performed at 80° C. After distilling off the solvent, distillation was carried out to thereby give 95 g of the purified product.

[α]D 24: +3.7° (c 1.0, $CHCl_3$).
$^1$H-NMR (400 MHz, $CDCl_3$, ppm):
0.85 (m, 1H), 0.89 (d, 6H), 0.92 (d, 3H), 1.12–1.23 (m, 2H), 1.44 (ddd, 1H), 1.49–1.65 (m, 3H), 1.77 (m, 1H), 3.29 (m, 1H), 3.38 (ddd, 1H), 3.97 (ddd, 1H).

MS (m/e): 156 ($M^+$), 99, 81, 69, 57, 55, 43, 42, 41, 39.
IR ($cm^{-1}$): 2950, 1460, 1095.

SYNTHESIS EXAMPLES 3 TO 8

Starting from (S)-citronellol or (R)-citronellol, syntheses were performed in accordance with the method of *J. Org. Chem.,* 35, 1097 (1970) while altering the reaction conditions. After purifying by fine distillation, the following isomers were obtained. Now, the properties of these isomers will be illustrated.

Rose oxide (3) (4R)-trans [(2R,4R)]:

[α]D 24: −2.9° (c 1.4, $CHCl_3$).

$^1$H-NMR (400 MHz, $CDCl_3$, ppm):

1.07 (d, 3H), 1.25 (m, 1H), 1.37 (m, 1H), 1.59 (ddd, 1H), 1.70 (d, 3H), 1.72 (d, 3H), 1.76 (m, 3H), 2.02 (m, 1H), 3.67–3.78 (m, 2H), 4.37 (dt, 1H), 5.29 (m, 1H).

MS (m/e): 154 ($M^+$), 139, 83, 69, 55, 41, 39.

IR ($cm^{-1}$): 2925, 1670, 1080.

(4) (4S)-cis [(2R,4S)]:

[α]D 25: +78.7° (c 1.0, $CHCl_3$).

(5) (4S)-trans [(2S,4S)]:

[α]D 25: +3.2° (c 1.1, $CHCl_3$).

Dihydrorose oxide (6) (4R)-2H-trans [(2S,4R)]:

[α]D 25: −11.8° (c 1.0, $CHCl_3$).

$^1$H-NMR (400 MHz, $CDCl_3$, ppm):

0.90 (d, 6H), 1.04 (d, 3H), 1.09 (ddd, 1H), 1.26 (m, 1H), 1.35 (m, 1H), 1.42–1.57 (m, 2H), 1.68–1.81 (m, 2H), 2.01 (m, 1H), 3.60–3.73 (m, 3H).

MS (m/e): 156 ($M^+$), 99, 81, 69, 57, 55, 43, 42, 39.

IR ($cm^-$): 2950, 1460, 1095

(7) (4S)-2H-cis [(2S,4S)]:

[α]D 25: −3.5° (c 1.0, $CHCl_3$).

(8) (4S)-2H-trans [(2R,4S)]:

[α]D 25: +11.0° (c 1.1, $CHCl_3$).

[Test Example 1]

Determination of odor threshold values and odor descriptions

The odor threshold values and odor descriptions were determined by the triangular system reported by T. E. Acree et al., *J. Agric. Food. Chem.,* 33, 425 (1985) by employing 11 to 13 panelists. Each sample was dissolved in 95% ethanol and then diluted with distilled water so as to give a definite concentration.

Table 1 shows the results of the determination of the odor threshold values while Table 2 shows the results of the evaluation of the odor descriptions.

TABLE 1

| No. | Compound | Threshold |
|---|---|---|
| (1) | 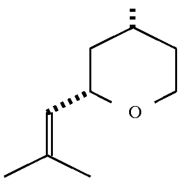 (4R)-cis | 0.5 ppb |

TABLE 1-continued

| No. | Compound | Threshold |
|---|---|---|
| (2) | 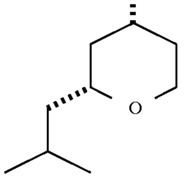 (4R)-2H-cis | 17 ppb |
| (3) | 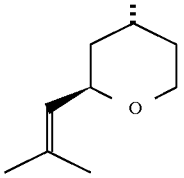 (4R)-trans | 160 ppb |
| (4) | 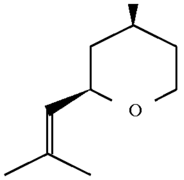 (4S)-cis | 50 ppb |
| (5) | 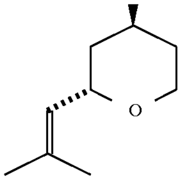 (4S)-trans | 80 ppb |
| (6) | 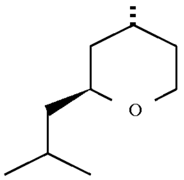 (4R)-2H-trans | 150 ppb |
| (7) | 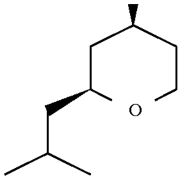 (4S)-2H-cis | 450 ppb |
| (8) | 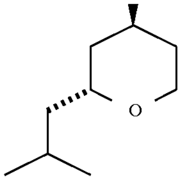 (4S)-2H-trans | 160 ppb |

TABLE 2

| No. | Compound | Fragrance qualities |
|---|---|---|
| (1) | 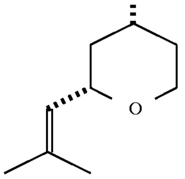 (4R)-cis | floral green clean, sharp light, rose green, diffusible, strong |
| (2) | 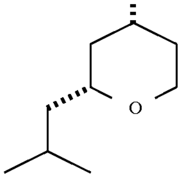 (4R)-2H-cis | floral green clean, ripe fruit herbal, rose green, leafy |
| (3) | 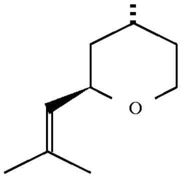 (4R)-trans | floral green green herbal (minty), fruity |
| (4) | 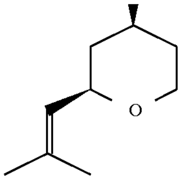 (4S)-cis | herbal green floral hay green, earthy, heavy |
| (5) | 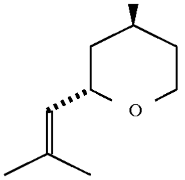 (4S)-trans | herbal green floral fruity, herbal rose, citras (bitter peel) |
| (6) | 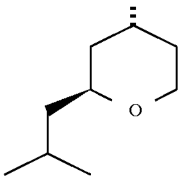 (4R)-2H-trans | herbal floral fruity, minty, dusty floral green |
| (7) | 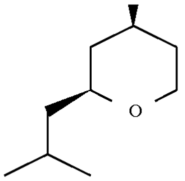 (4S)-2H-cis | herbal green herbal, leafy green heavy |

TABLE 2-continued

| No. | Compound | Fragrance qualities |
|---|---|---|
| (8) | 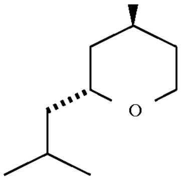 (4S)-2H-trans | herbal green citrus fruity, herbal, fresh citrus (grapefruit) |

As Tables 1 and 2 show, in both of rose oxide and dihydrorose oxide, the (4R)-cis-isomers are superior to other isomers because of having an intense fragrance with a sharp, clean and rose green note.

[Test Example 2]

Biodegradation test

By using activated sludge [obtained on Jan. 20, 1994 from Zaidan-hojin Kagakuhin Kensa Kyokai (Association of Inspection on Chemicals)], the test was performed in accordance with "Biodegradability test of chemicals by microorganisms, etc." specified in "Methods of tests relating to novel chemicals" [Kanpogyo No. 5 (the Environmental Agency), Yakuhatsu No. 615 (the Japanese Ministry of Health and Welfare), 49 Kikyoku No. 392 (the Japanese Ministry of International Trade and Industry), Jul. 13, 1974].

| | |
|---|---|
| Sample concentration: | 30 mg/liter |
| Activated sludge concentration: | 100 mg/liter |
| Test period: | 25 days |

The measurement was made on the (4R)-isomers [(4R)-cis/(4R)-trans=71/29)] and the (4S)-isomers [(4S)-cis/(4S)-trans=71/29)] of rose oxide. The (4R)-isomers degraded at a ratio of 90% within 28 days, while the (4S)-isomers scarcely degraded. Detailed examination on the (4R)-isomers indicated that the (4R)-trans-isomer remained in a small amount. It has been thus proved that the (4R)-cis-isomer has the highest biodegradability.

EXAMPLE 1

Perfume compositions were prepared in accordance with the following formulations. The amount of each component is expressed in parts by weight.

| Cologne for man | |
|---|---|
| cis-(2S,4R)-rose oxide | 15 |
| ambroxan | 3 |
| α-damascone (10% soln. in dipropylene glycol) | 6 |
| armoise oil (10% soln. in dipropylene glycol) | 8 |
| basil oil | 26 |
| benzyl salicylate | 150 |
| bergamot fl-gc | 150 |
| clary sage ABS | 15 |
| clove bat oil | 10 |
| coumarin | 25 |
| dihydromyrcenol | 120 |
| methyl dihydrojasmonate | 201 |
| lavender ABS | 6 |
| lemon oil | 30 |
| linalol | 25 |
| oakmoss ABS | 20 |
| patchouli light | 70 |

-continued

| | |
|---|---|
| 7-acetyl-1,1,3,4,4,6-hexamethyltetralin | 50 |
| acetylcedrene | 70 |
| total | 1,000 |

Aldehyde bouquet (for soap)

| | |
|---|---|
| cis-(2S,4R)-rose oxide | 10 |
| $\alpha$-damascone (10% soln. in dipropylene glycol) | 10 |
| aldehyde C-10 (10% soln. in dipropylene glycol) | 5 |
| aldehyde C-11 | 5 |
| aldehyde C-12 (50% soln. in benzyl, benzoate) | 6 |
| bergamot | 20 |
| coumarin | 60 |
| cyclamen aldehyde | 8 |
| geranium | 16 |
| p-t-butyl-$\alpha$-methylhydrocinnamicaldehyde | 70 |
| tetrahydrolinalol | 100 |
| linalol | 80 |
| linalyl acetate | 30 |
| p-t-butylcyclohexyl acetate | 140 |
| patchouli oil | 18 |
| raspberry ketone (10% soln. in dipropylene glycol) | 10 |
| rose base | 250 |
| rose phenone | 20 |
| isobornylcyclohexanol | 60 |
| styrallyl acetate | 8 |
| 7-acetyl-1,1,3,4,4,6-hexamethyltetralin | 60 |
| 4-(4-methyl-3-pentenyl)-3-cyclohexenecarbaldehyde | 14 |
| total | 1,000 |

Natural-type rose

| | |
|---|---|
| cis-(2S,4R)-rose oxide | 3 |
| $\alpha$-damascone (10% soln. in dipropylene glycol) | 8 |
| aldehyde C-9 (10% soln. in dipropylene glycol) | 10 |
| $\beta$-ionone | 18 |
| cis-3-hexenyl acetate | 1 |
| eugenol | 4 |
| geraniol | 110 |
| geranyl acetate | 7 |
| phenylacetaldehyde (50% soln. in benzyl benzoate) | 20 |
| ionone SP | 8 |
| isocyclocitral | 3 |
| L-citronellol | 110 |
| citronellyl acetate | 8 |
| citronellyl formate | 3 |
| cis-3-hexenol | 2 |
| methyleugenol | 10 |
| nerol | 20 |
| phenylethyl alcohol | 480 |
| phenylethyl acetate | 70 |
| 9-decen-1-ol (10% soln. in dipropylene glycol) | 5 |
| total | 900 |

Fresh green type (for multi-purpose cleaner)

| | |
|---|---|
| cis-(2S,4R)-rose oxide | 0.4 |
| amyl salicylate | 30 |
| calamus oil | 0.4 |
| dipropylene glycol | 70 |
| galbanum oil | 1.2 |
| 3,4-methylenedioxy-$\alpha$methylhydrocinnamic aldehyde | 10 |
| 4-(4-hydroxy-4-methylpentyl)-3-cyclohexenecarbaldehyde | 100 |
| L-citronellol | 8 |
| citral | 20 |
| lemon oil | 100 |
| p-t-butyl-$\alpha$-methylhydrocinnamic aldehyde | 94 |
| tetrahydro mugol | 100 |
| linalyl acetate | 150 |
| methyl naphthyl ketone | 20 |
| ethylene brassylate | 90 |
| 1-(2,2,6-trimethylcyclohexyl)-3-hexanol | 1 |
| petitgrain oil | 15 |
| phenylethyl alcohol | 15 |
| p-isobutyl-$\alpha$-methylhydrocinnamic aldehyde | 20 |

-continued

| | |
|---|---|
| 7-acetyl-1,1,3,4,4,6-hexamethyltetralin | 40 |
| dimethyltetrahydrobenzaldehyde | 15 |
| total | 900 |

As a result, the cologne for man, the aldehyde bouquet, the natural type rose and the fresh green type were highly evaluated respectively because of having sharp top note and light green accent,.serving as the reinforcement for the green body note, and having an improved natural feel. Namely, each of these compositions had a fragrance having a highly preferable freshness, a refreshing feel and a rose green note.

Similarly, compositions were prepared by using cis-(2R, 4R)-dihydrorose oxide as a substitute for the cis-(2S,4R)-rose oxide. The compositions thus obtained were almost comparable to the above-mentioned ones containing cis-(2S, 4R)-rose oxide, though they had somewhat weaker rose green notes.

While the invention has been described in detail and with reference to specific embodiments thereof, it will be apparent to one skilled in the art that various changes and modifications can be made therein without departing from the spirit and scope thereof.

What is claimed is:

1. A perfume composition comprising a (4R)-cis-4-methyl-2-substituted-tetrahydro-2H-pyran derivative represented by formula (I):

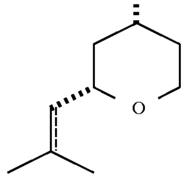

(I)

wherein ═══ represents a single or double bond; and wherein said (4R) -cis-4-methyl-2-substituted-tetrahydro-2H-pyran derivative has a chemical purity of at least 90% by weight and an optical purity of at least 95% ee.

2. A method for improving a fragrance by using a (4R) -cis-4-methyl-2-substituted-tetrahydro-2H-pyran derivative represented by formula (I):

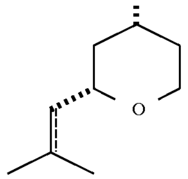

(I)

wherein ═══ represents a single or double bond; and wherein said (4R)-cis-4-methyl-2-substituted-tetrahydro-2H-pyran derivative has a chemical purity of at least 90% by weight and an optical purity of at least 95% ee.

3. The perfume composition as claimed in claim 1 wherein the content of said (4R)-cis-4-methyl-2-substituted-tetrahydro-2H-pyran derivative ranges from 0.01 to 30% by weight.

4. A method for improving a fragrance with preferable freshness, a refreshing feel and a rose green note by using the perfume composition of claim 1.

5. A method for improving a fragrance with preferable freshness, a refreshing feel and a rose green note by adding the perfume composition of claim 1 to hair care products, cosmetic bases, cosmetic cleaners and sanitary detergents.

6. A method for improving a fragrance as in claim 4, wherein said hair care products, cosmetic bases, cosmetic cleansers or sanitary detergents are ones selected from the group consisting of a shampoo, rinse, perfume, hair cologne, hair tonic, hair cream, pomade, face powder, lipstick, soap, kitchen detergent, laundry detergent, softener, disinfectant detergent, deodorizer, room aromatic, furniture care, disinfectant bactericide and bleach.

* * * * *